(12) United States Patent
Trubey

(10) Patent No.: US 10,186,135 B2
(45) Date of Patent: Jan. 22, 2019

(54) WEARABLE CHEMICAL THREAT DETECTOR

(71) Applicant: Goodrich Corporation, Charlotte, NC (US)

(72) Inventor: Richard K. Trubey, Upland, CA (US)

(73) Assignee: Goodrich Corporation, Charlotte, NC (US)

( * ) Notice: Subject to any disclaimer, the term of this patent is extended or adjusted under 35 U.S.C. 154(b) by 0 days.

(21) Appl. No.: 15/383,819

(22) Filed: Dec. 19, 2016

(65) Prior Publication Data

US 2018/0174423 A1 Jun. 21, 2018

(51) Int. Cl.
| G08B 21/12 | (2006.01) |
| G01N 33/00 | (2006.01) |
| G08B 25/08 | (2006.01) |

(52) U.S. Cl.
CPC ......... *G08B 21/12* (2013.01); *G01N 33/0031* (2013.01); *G01N 33/0062* (2013.01); *G01N 33/0075* (2013.01); *G08B 25/08* (2013.01)

(58) Field of Classification Search
None
See application file for complete search history.

(56) References Cited

U.S. PATENT DOCUMENTS

| 7,834,320 B2 | 11/2010 | Goldberg et al. |
| 7,837,844 B2 | 11/2010 | Patel et al. |
| 7,843,356 B2 | 11/2010 | Webb |
| 7,965,089 B2 | 6/2011 | Bonne et al. |
| 8,618,934 B2 | 12/2013 | Belov et al. |
| 8,994,546 B2 | 3/2015 | Breed et al. |

(Continued)

FOREIGN PATENT DOCUMENTS

WO WO-2015/160830 A1 10/2015

OTHER PUBLICATIONS

Seesaard Thara et al., "A Novel Creation of Thread-Based Ammonia Gas Sensors for Wearable Wireless Security System", 2014 11th International Conference on Electrical Engineering/Electronics, Computer, Telecommunications and Information Technology (ECTI-CON), IEEE, May 14, 2014, pp. 1-4.

(Continued)

*Primary Examiner* — Emily C Terrell
(74) *Attorney, Agent, or Firm* — Locke Lord LLP; Scott D. Wofsy; Joshua L. Jones

(57) ABSTRACT

The present disclosure generally relates to chemical threat detection, and more specifically, to a wearable chemical threat detector for an indoor or outdoor environment. In one embodiment, a method for chemical sensing and detection is disclosed. The method includes (a) deploying a plurality of wearable chemical detectors, (b) receiving an environmental air sample by at least one of the plurality of wearable chemical detectors, (c) receiving an alert of one or more chemical(s) present within the environmental air sample from at least one wearable chemical detector, (d) analyzing the alert for data relating to at least one of a chemical name, a chemical concentration, a chemical category, or a toxicity level, and (e) transmitting the data to a central data collection site. Furthermore, the embodiments disclosed may provide a warning and/or an evacuation route to a user once a threat is detected.

17 Claims, 3 Drawing Sheets

(56) References Cited

U.S. PATENT DOCUMENTS

| | | | | |
|---|---|---|---|---|
| 9,013,297 | B1* | 4/2015 | Dey | A42B 3/046 340/539.11 |
| 9,103,775 | B2 | 8/2015 | Bradley et al. | |
| 2004/0135684 | A1* | 7/2004 | Steinthal | B82Y 30/00 340/522 |
| 2006/0017579 | A1* | 1/2006 | Albert | G04G 13/021 340/628 |
| 2008/0088434 | A1* | 4/2008 | Frieder | G08B 21/12 340/539.11 |
| 2008/0146892 | A1* | 6/2008 | LeBoeuf | A61B 5/0205 600/300 |
| 2008/0311882 | A1* | 12/2008 | Schlager | A61N 1/08 455/404.2 |
| 2015/0022357 | A1* | 1/2015 | Gettings | G01N 21/84 340/568.1 |
| 2015/0157261 | A1 | 6/2015 | Sakagami | |
| 2016/0335865 | A1* | 11/2016 | Sayavong | G08B 13/2491 |

OTHER PUBLICATIONS

Huo Zhiqiang et al., "Cloud-Based Data-Intensive Framework Towards Fault Diagnosis in Large-Scale Petrochemical Plants", 2016 International Wireless Communication and Mobile Computing Conference (IWCMC), IEEE, Sep. 5, 2016, pp. 1080-1085.

Chung-Chuo Wu et al., "An Intelligent Active Alert Application on Handheld Devices for Emergency Evacuation Guidance", 2013 Fifth International Conference on Ubiquitous and Future Networks (ICUFN), IEEE, Jul. 2, 2013, pp. 7-11.

Extended European Search Report dated Apr. 24, 2018 issued during the prosecution of European Patent Application No. EP 17208562.3 (12 pages).

* cited by examiner

WEARABLE CHEMICAL THREAT DETECTOR

BACKGROUND OF THE INVENTION

1. Field of the Invention

The present disclosure generally relates to chemical detection, and more particularly to a wearable chemical threat detector which provides a user with an alert and/or instruction.

2. Description of Related Art

Chemical threat detection generally relates to the recognition of and alert to of any number of known toxic chemical vapors in the environmental background. Military and homeland security applications include the detection of chemical warfare agents and toxic industrial chemicals used by enemy states or terrorists to intentionally harm military troops or civilians abroad or in the U.S. Chemical munitions left behind from old conflicts routinely present a chemical hazard to the military. The ability to detect toxic chemicals is important in a variety of other contexts, including the detection of potentially toxic chemicals in a home, business, or factory to prevent fire, injury, death, or health problems. The early detection of chemical agents and toxic chemical vapors in general may provide an opportunity to warn military personnel or the public in sufficient time to provide an opportunity for appropriate evacuation, personal protection by donning protective equipment, or containment of the chemical threat source.

Typical chemical threat detectors are heavy and complex, thus making it difficult to transport and deploy multiple devices in large groups. Furthermore, typical costs for chemical threat detectors prohibit wide spread deployment to multiple users. Also, there is a tradeoff between achieving sensitive chemical detection and producing accurate chemical detection results that reduce false positive rates. The conventional techniques have been considered satisfactory for their intended purpose. However, there is an ever present need for an improved wearable chemical threat detector. This disclosure provides a solution for this need.

SUMMARY OF THE INVENTION

The present disclosure generally relates to chemical threat detection, and more specifically, to a wearable chemical threat detector. In one embodiment, a method for chemical sensing and detection is disclosed. The method includes (a) deploying a plurality of wearable chemical detectors, (b) receiving an environmental air sample by at least one of the plurality of wearable chemical detectors, and (c) receiving an alert of one or more chemicals present within the environmental air sample from at least one wearable chemical detector. The method also includes (d) analyzing the alert for data relating to at least one of a chemical name, a chemical concentration, a chemical category, or a toxicity level, and (e) transmitting the data to a central data collection site. In certain embodiments, the method can also include receiving an instruction by at least one wearable chemical threat detector for a user to follow. The instruction can relate to threat detection. In some embodiments, the instruction can relate to an escape trajectory for exiting an environment containing the detected chemical(s), or can triangulate and communicate a location source of the detected chemical(s) from a plurality of wearable chemical threat detectors. Also, in some embodiments, the instruction can be received by more than one chemical detector, the instruction can determine whether an alert of a detected chemical(s) is a false positive, or the instruction can relate to an action to be performed by a user, such as a health preventative action, for example donning a respirator.

In another embodiment, a system for detecting chemicals is disclosed. The system includes a housing, a gas sampling chamber disposed within the housing, a sensor operatively connected to or contained within the gas sampling chamber, and a power management system disposed within the housing and operatively connected to the sensor. The system also includes a controller operatively connected to the sensor. The detection system includes a processor, e.g., a microprocessor, and a memory, e.g., a solid state memory. The memory stores instructions that, when executed by the processor, cause the system to receive an environmental air sample within the gas sampling chamber, receive an alert by the sensor of one or more chemicals detected within the environmental air, analyze the alert for data relating to at least one of a chemical name, a chemical concentration, a chemical category, or a toxicity level, and transmit the data to a central data collection site. In some embodiments, the sensor can include an array of up to about 16 chemically tailored nanosensors, and the array can be supported on a microelectromechanical system consisting of an electrical resistance transducer platform. Also, in certain embodiments, each nanosensor can have a surface coating (for example, carbon nanotube, nanofiber, or nanowire technology, molecularly imprinted polymers, metal-organic frameworks or other nanoparticle technologies) enabling sensing of particular chemicals or classes of chemicals disposed thereon. In embodiments, an electrochemical response (e.g., voltage or current) can be used as the basis for sensor outputs. In embodiments, surface acoustic wave phenomena can be used as the basis for sensor outputs. In embodiments, colorimetric phenomena can be used as the basis for sensor outputs. In embodiments, immunochemical (e.g., antibody-antigen) phenomena can be used as the basis for sensor outputs. In embodiments, the system can also include an alert mechanism configured to provide a status (for example, detected or not detected, chemical identity, concentration, hazard severity, or the like) of detected chemical(s) present. The alert mechanism can be a visual indicator, an audible indicator, or a vibratory indicator, and in certain embodiments, the alert mechanism can provide the status of the detected chemical(s) present in real time. Additionally, in some embodiments, the system can further include a pump for circulating environmental air samples into and out of the gas sampling chamber and/or a graphical user interface operatively connected to the housing and the controller and configured to display the information to a user.

These and other features of the methods and systems of the subject disclosure will become more readily apparent to those skilled in the art from the following detailed description of the preferred embodiments taken in conjunction with the drawings.

BRIEF DESCRIPTION OF THE DRAWINGS

So that those skilled in the art to which the subject disclosure appertains will readily understand how to make and use the devices and methods of the subject disclosure without undue experimentation, preferred embodiments thereof will be described in detail herein below with reference to certain figures, wherein.

DETAILED DESCRIPTION OF THE PREFERRED EMBODIMENTS

Figure 1A:
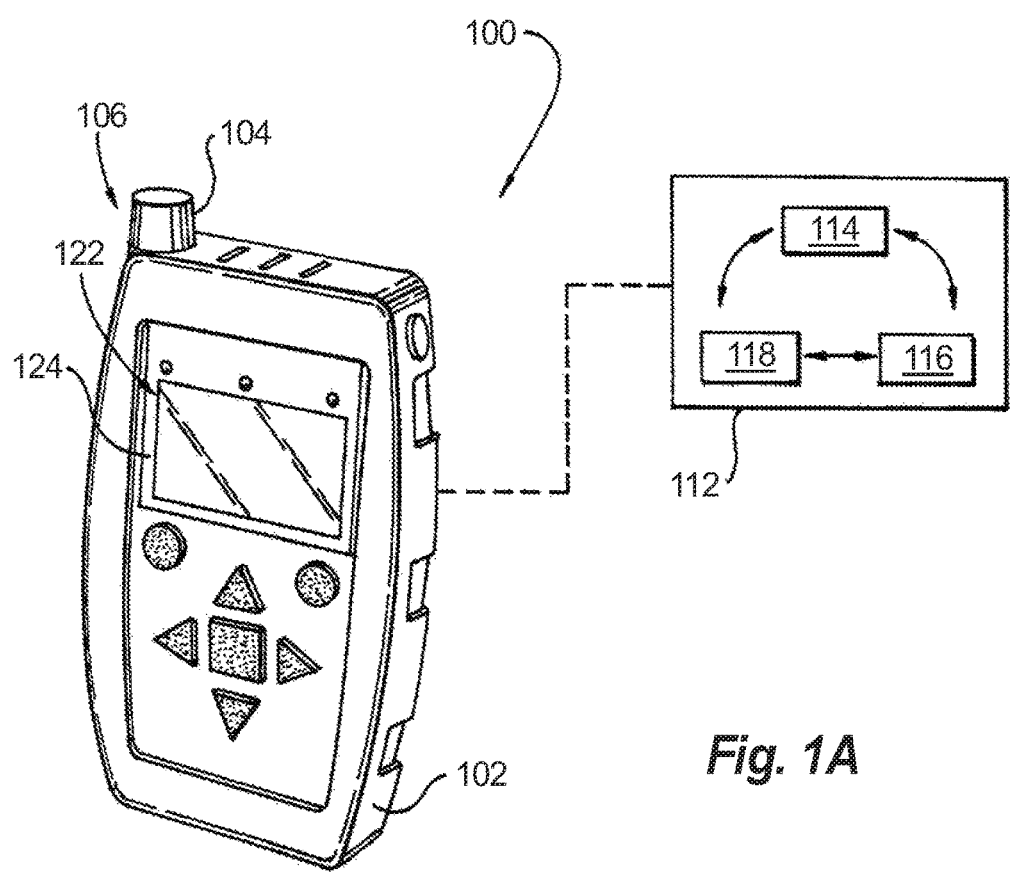
FIG. 1A is a front schematic perspective view of a system for chemical threat detection, constructed in accordance with an exemplary embodiment of the present disclosure, showing a gas sample intake (e.g., actively pumped) and a graphical user interface.
Figure 1B:
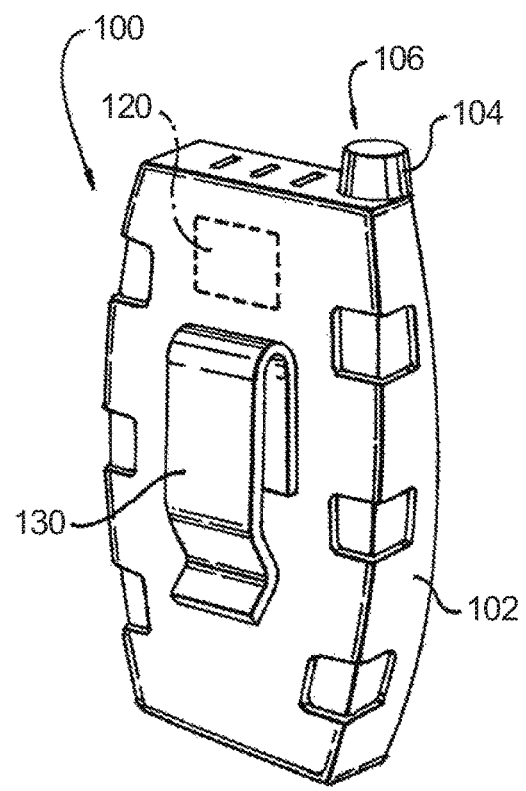
FIG. 1B is a back schematic perspective view of the system of FIG. 1A.
Figure 2:
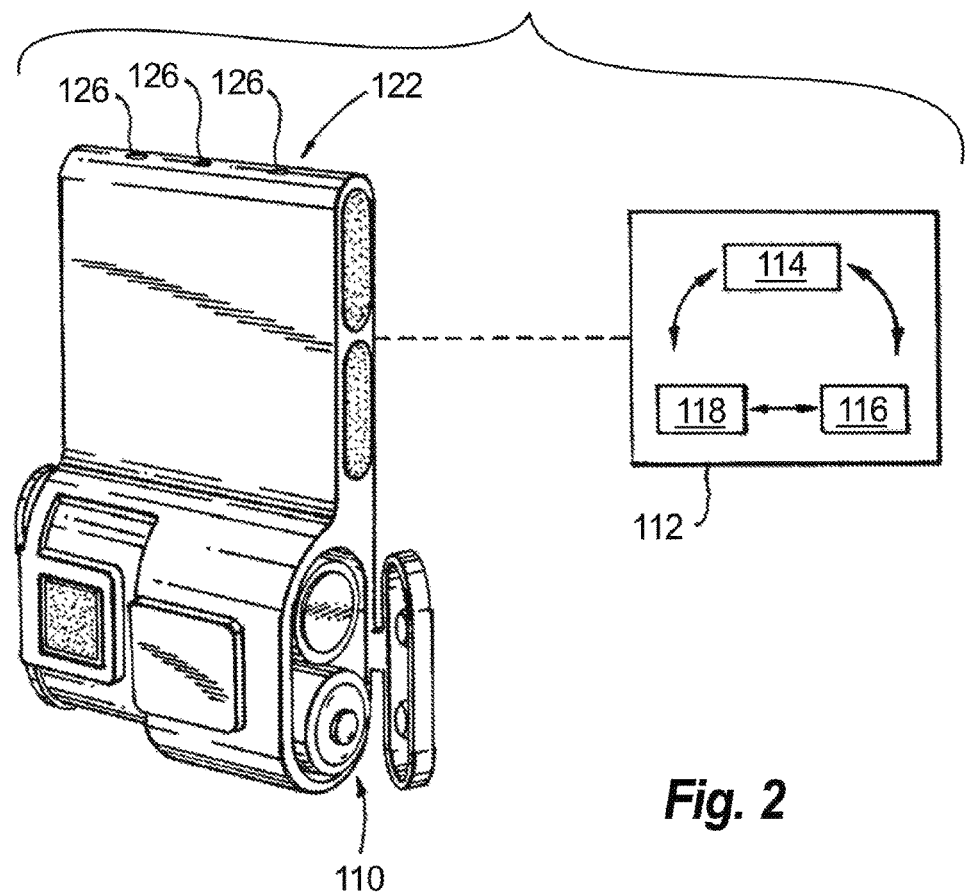
FIG. 2 is a front schematic perspective view of another exemplary embodiment of the system for chemical threat detection having a passive gas sample intake (e.g., no pumping required) and an LED light alert indicator.

Reference will now be made to the drawings wherein like reference numerals identify similar structural features or aspects of the subject disclosure. For purposes of explanation and illustration, and not limitation, a partial view of an exemplary embodiment of the chemical detection system in accordance with the disclosure is shown in FIGS. 1A, 1B, and 2 and is designated generally by reference character 100. Other embodiments of systems in accordance with the disclosure, or aspects thereof, are provided in FIG. 4, as will be described. The systems and methods described herein can be used to provide a warning, a triangulation of a source, and/or an evacuation route to a user once a threat is detected.

The term "user" as used herein includes, for example, a person or entity that owns a computing device, wireless device, and/or chemical detector device; a person that operates or utilizes said device(s); or a person or entity that is otherwise associated with said device(s). It is contemplated that the term "user" is not intended to be limiting and may include various examples beyond those described.

Figure 3:
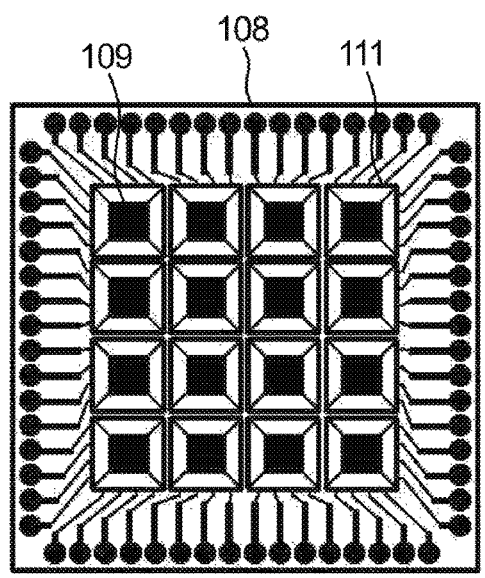
FIG. 3 is a schematic view of a sensor for use in the system of FIG. 1.

As shown in FIGS. 1A, 1B, and 2 the system 100 for chemical detection includes a housing 102 and a gas sampling chamber 104 disposed within the housing 102. The gas sampling chamber 104 has an opening 106 therein which exposes the gas sampling chamber 104 to the ambient air environment. Exposure of the gas sampling chamber 104 to the environment via the opening 106 allows environmental gases (e.g., air, other gases, and/or chemical vapors) to enter the gas sampling chamber 104. As shown in FIG. 3, the system 100 also includes a sensor 108. The sensor 108 includes an array of up to 16 chemically tailored nanosensors 109. In certain embodiments, the nanosensors 109 may be supported on a platform 111. Each nanosensor 109 includes a chemically-specific surface coating that interacts with a particular target gas or vapor. When a particular nanosensor 109 interacts with a specific chemical, the electrical resistance of said nanosensor is altered by either an increase or decrease. When a particular nanosensor 109 reacts to a specific target gas (while other nanosensors may not react) the electrical resistance of the nanosensor 109 may change in a predictable manner as a result of the gas-sensor interaction. Response signals may be evaluated by a suite of algorithms that process and interpret each nanosensor's 109 response characteristics to provide autonomous, real-time, and continuous detection and identification of target gases. In certain embodiments, the algorithms include pre-processing, hit detection, classification, identification, and/or concentration measurement. The algorithms process and interpret nanosensor 109 response characteristics to provide autonomous and continuous, near-real-time detection of the desired target gases/vapors, e.g., to detect at least one chemical from a selected set of possible chemicals.

Returning to FIGS. 1A, 1B, and 2, the system further includes a power management system 110, and a controller 112. The sensor 108 is operatively connected to the gas sampling chamber 104. The power management system 110 is disposed within the housing 102 and is operatively connected to the sensor 108.

The controller 112 is operatively connected to the sensor 108. The controller 112 includes at least one central processing unit (CPU) 114 and one or more memory integrated circuits (ICs) 116. The memory IC 116 stores instructions that, when executed by the CPU 114, cause the system 100 to receive an environmental air sample within the gas sampling chamber 104, receive an alert by the sensor 108 of a detected chemical(s) present within the ambient environmental air, and analyze the alert for data relating to at least one of a chemical name, a chemical concentration, a chemical category, or a toxicity level. The instructions stored by the memory ICs 116, when executed by the CPU 114, further cause the system 100 to transmit the data to a central data collection site.

The controller 112 also includes support circuits (or I/O) 118. The CPU 114 may be one of any form of computer processors that are used in industrial settings for controlling various processes and hardware (e.g., motors or other hardware) and monitor the processes (e.g., air sample within the gas sampling chamber, sensor, data, etc.). The memory 116 is connected to the CPU 114, and may be one or more of a readily available memory, such as random access memory (RAM), read only memory (ROM), or any other form of digital storage, local or remote. Software instructions and data can be coded and stored within the memory 116 for instructing CPU 114. The support circuits 118 are also connected to the CPU 114 for supporting the CPU 114 in a conventional manner. The support circuits 118 may include conventional cache, power supplies, clock circuits, input/output circuitry, subsystems, and the like. A program (or computer instructions) readable by the controller 112 implements the method described herein (infra) and/or determines which tasks are performable. The program may be software readable by the controller 112 and may include code to monitor and control, for example, environmental air sample intake, alerts, data, transmissions, etc. In certain embodiments, the controller 112 may be a PC microcontroller. The controller 112 may also automate the sequence of the process performed, and/or the modes performed, by the system for chemical detection.

In certain embodiments, the system 100 further includes a pump 120 (shown in phantom) disposed therein. In some embodiments, the pump 120 is operatively connected to the gas sampling chamber 104. The pump 120 may circulate an environmental air sample into and/or out of the gas sampling chamber 104. As such, the pump 120 may operate to continuously draw ambient environmental air across the sensor in order to expose the nanosensor array to the ambient air. In certain embodiments, a temperature and/or humidity sensor are also disposed within the housing 102 in order to monitor local conditions and provide feedback to the algorithms such that local environmental conditions may be compensated for. Furthermore, in some embodiments, a clip 130 may be operatively connected to the housing 102. The clip 130 may allow a user to attach the system 100 to their belt, other equipment, or the like.

In some embodiments, the system 100 operates autonomously and/or continuously while providing real-time sensor signal outputs. Sensor signal outputs may include an alert provided by an alert mechanism 122. The alert mechanism 122 is configured to provide a status of detected chemical(s) present to a user. The alert mechanism 122 may be a visual indicator, an audible indicator, or a vibratory indicator, among other indicators known in the art. In some embodiments, the alert mechanism 122 may be a graphical user interface, such as graphical user interface 124 shown in FIG. 1, while in other embodiments the alert mechanism 122 may be a light, such as LED lights 126 in FIG. 2. The graphical user interface 124 may be operatively connected to the housing 102 and the controller 112. The graphical user interface 124 is configured to display information to the user.

The alert mechanism 122 provides the status of the detected chemical(s) present in real time to the user. Furthermore, in some embodiments as discussed infra, the alert mechanism 122 may provide evacuation instructions to a user, may triangulate the source and/or location of the chemical to the user, may provide safety instructions to the user (e.g., relating to the use of required safety equipment), and/or may alert the user to the chemical name, the chemical concentration, the chemical category, and/or the chemical toxicity level.

Figure 4:
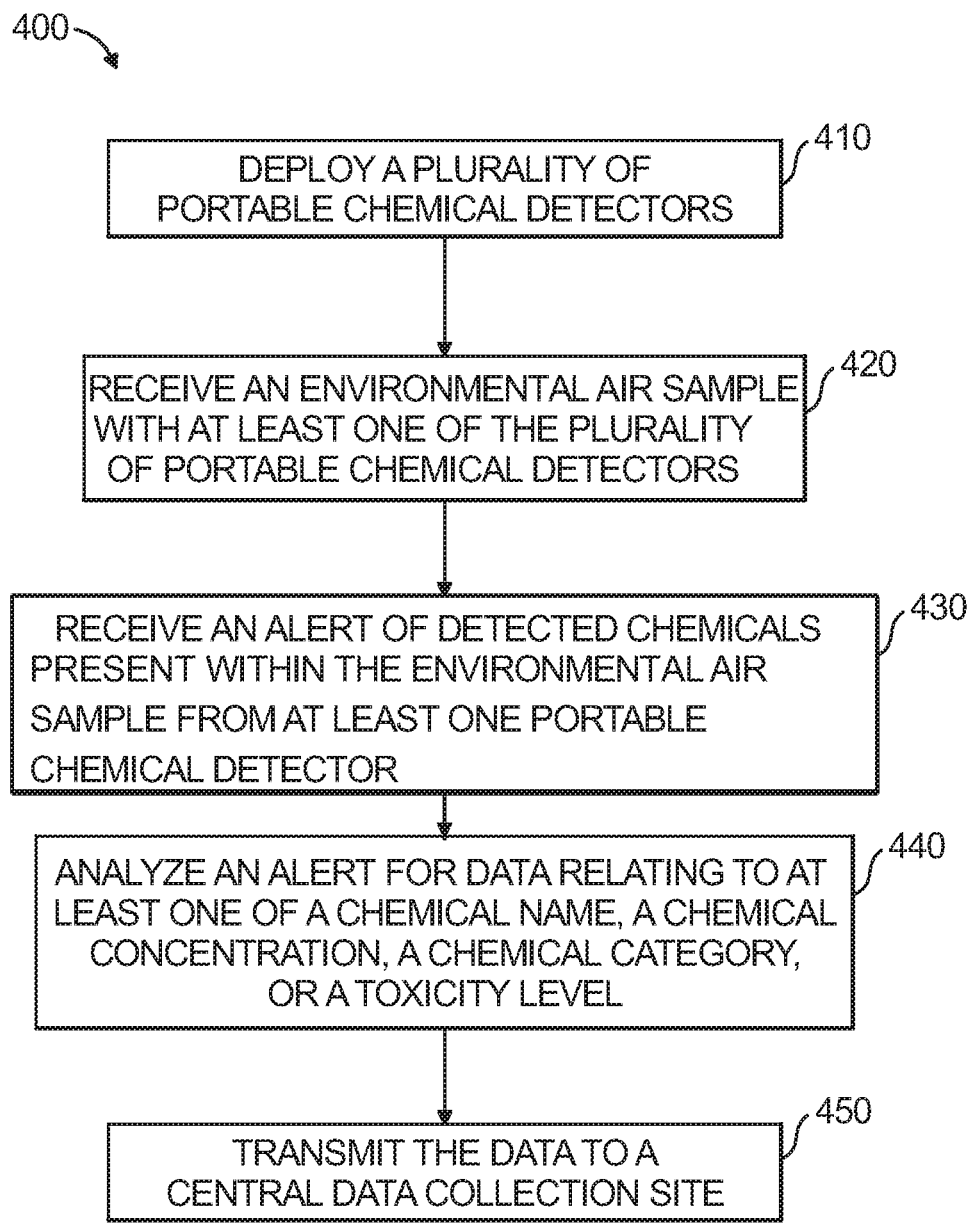
FIG. 4 is a schematic flow diagram of a method for chemical sensing, in accordance with an exemplary embodiment of the present disclosure.

FIG. 4 illustrates a schematic flow diagram of a method 400 for chemical sensing. At operation 410, a plurality of wearable chemical detectors are deployed. In certain embodiments, the deployment may be outside, while in other embodiments the deployment may be indoors. Deployment may include equipping a user, or multiple users, with a wearable chemical detector.

At operation 420, an environmental air sample is received by at least one of the plurality of wearable chemical detectors. As discussed supra, environmental air may be circulated into and out of the gas sampling chamber via the pump. A sensor disposed within the wearable chemical detector may determine the presence and concentration of one or more chemicals, toxic gases, or the like.

At operation 430, an alert of a detected chemical(s) present within the environmental air sample is received by at least one wearable portable chemical detector. The alert may be in one of various forms. In some embodiments, the alert may be a visual alert via, for example, an LED or a graphical user interface, while in other embodiments, the alert may be an audible alert. In some embodiments, the alert may be vibratory or any other suitable alert scheme.

At operation 440, the alert is analyzed for data relating to at least one of a chemical name, a chemical concentration, a chemical category, and/or a toxicity level. In certain embodiments, the analyzed data may be disposed on the graphical user interface.

At operation 450, the data is transmitted to a central data collection site. The central data collection site may be a server, a hard drive, a computer, or the like that is onsite or offsite. In certain embodiments, any of operation 410, operation 420, operation 430, operation 440, and/or operation 450 may be repeated until a detected chemical is no longer detected. As such, each wearable chemical detector may operate autonomously and/or continuously to provide real-time sensor signal outputs and/or instructions to the user.

In some embodiments, the method 400 further includes receiving an instruction by at least one wearable chemical detector, wherein the instruction is for a user to follow. The instruction may relate to threat detection. A threat may be detected when one or more chemical(s) is/are in the environmental air sample received by at least one of the wearable chemical detectors. The threat may make it unsafe for a user to be in the area without proper personal safety protections.

Furthermore, the instruction may relate to an escape trajectory for exiting an environment containing the detected chemical(s). As such, the instruction may guide the user, via a visual indication or an audible indication, to an escape path for safely leaving the contaminated area. In other embodiments, the instruction may triangulate and communicate the location source of the detected chemical(s) from a plurality of the wearable chemical detectors. For example, when multiple wearable chemical detectors are being utilized in approximately the same general area, each portable chemical detector is configured to communicate with one another. The communication may occur via a peer-to-peer network, over internet connection, via Bluetooth connection, or the like. Detector communication may be facilitated by mobile telephones, radios, or the like, that the user is also wearing. Each communicating wearable chemical detector may communicate information relating to, for example, chemical concentrations measured. Such communications may allow the source or location of the detected chemical(s) to be determined, for example by triangulation, such that the threat can be eliminated. In certain embodiments, the instruction may relate to an action to be performed by a user. In some embodiments, the action may be a health preventative action, such as an instruction for the user to wear a protective respirator, protective clothing, or the like. For example, each wearable chemical detector may receive the instruction in order to direct the respective user away from the area of the detected chemical(s) or, in certain instances, to direct the respective user toward the source or plume of the detected chemical(s). In some embodiments, the instruction may communicate to the user whether the alert of a detected chemical is a false positive.

The methods and systems of the present disclosure, as described above and shown in the drawings, provide for an improved wearable chemical threat detector with superior properties including lighter overall weight, reduced production costs, increased detection speed, more reliable chemical identification and concentration determination, user instructions, improved usability, and reduced power consumption. While the apparatus and methods of the subject disclosure have been shown and described with reference to preferred embodiments, those skilled in the art will readily appreciate that changes and/or modifications may be made thereto without departing from the scope of the subject disclosure.

What is claimed is:

1. A method for detecting airborne chemicals, comprising:
    (a) utilizing multiple wearable chemical detectors in a single general area;
    (b) acquiring an environmental air sample within each wearable chemical detector;
    (c) detecting that at least one chemical from a selected set of possible chemicals is present within the environmental air sample;
    (d) analyzing data relating to the detecting;
    (e) determining at least one of a chemical name, a chemical concentration, a chemical category, or a toxicity level;
    (f) transmitting the determined information to a central data collection site;
    (g) each wearable chemical detector communicating with each other information relating to chemical concentrations measured to generate an instruction; and
    (h) receiving the instruction by at least one wearable chemical detector for a user to follow, wherein the instruction includes an indication of whether an alert from an alert mechanism on the at least one wearable chemical detector of one or more detected chemicals present is a false positive.

2. The method of claim 1, wherein the instruction relates to threat detection.

3. The method of claim 1, wherein the instruction relates to an escape trajectory for exiting an environment containing the detected chemical(s).

4. The method of claim 1, wherein the instruction triangulates and communicates a location source of the detected chemical(s) determined from a plurality of wearable chemical detectors.

5. The method of claim 1, wherein the instruction is received by a plurality of chemical detectors.

6. The method of claim 1, wherein the instruction relates to an action to be performed by a user.

7. The method of claim 6, wherein the action is a health preventative action.

8. The method of claim 1, further comprising repeating (b)-(f) until one or more detected chemicals are no longer detected.

9. A wearable airborne chemical detecting system, comprising:
a housing;
a gas sampling chamber disposed within the housing;
a sensor operatively connected to the gas sampling chamber;
a power management system disposed within the housing and operatively connected to the sensor; and
a controller operatively connected to the sensor, comprising:
a processor; and
a memory integrated circuit (IC) storing instructions that, when executed by the processor, cause the system to:
acquire an environmental air sample within the gas sampling chamber;
electronically monitor the sensor for changes in resistance;
detect via the electronic monitoring that at least one chemical of a selected set of chemicals is present within the environmental air sample;
determine at least one of a chemical name, a chemical concentration, a chemical category, or a toxicity level;
transmit the determined information to a central data collection site;
utilize multiple wearable chemical detectors in a single general area, wherein the wearable chemical detector communicates with each other information relating to chemical concentrations measured to generate an instruction; and
receive the instruction by at least one wearable chemical detector for a user to follow, wherein the instruction includes an indication of whether an alert from an alert mechanism in the at least one chemical threat detector of one or more detected chemicals present is a false positive.

10. The system of claim 9, wherein the sensor comprises an array of up to about 16 chemically tailored nanosensors.

11. The system of claim 10, wherein the array is supported on a microelectromechanical system (MEMS) electrical resistance transducer platform.

12. The system of claim 10, wherein each nanosensor has a chemically-specific surface coating disposed thereon.

13. The system of claim 9, further comprising an alert mechanism, wherein the alert mechanism is configured to provide a status of a chemical detection event.

14. The system of claim 13, wherein the alert mechanism is a visual indicator, an audible indicator, or a vibratory indicator.

15. The system of claim 13, wherein the alert mechanism provides the status of detected chemical(s) present in real time.

16. The system of claim 9, further comprising a pump for circulating the environment air sample into and out of the gas sampling chamber.

17. The system of claim 9, further comprising a graphical user interface operatively connected to the housing and the controller, wherein the graphical user interface is configured to display information to a user.

* * * * *